US009096683B2

(12) United States Patent
Scheckermann et al.

(10) Patent No.: US 9,096,683 B2
(45) Date of Patent: Aug. 4, 2015

(54) METHOD FOR PURIFYING RECOMBINANT FSH

(75) Inventors: Christian Scheckermann, Ehrenkirchen/Ehrenstaetten (DE); Dietmar Eichinger, Schwetzingen (DE); Stefan Arnold, Schwetzingen (DE)

(73) Assignee: Ratiopharm GMBH, Ulm (DE)

( * ) Notice: Subject to any disclaimer, the term of this patent is extended or adjusted under 35 U.S.C. 154(b) by 112 days.

(21) Appl. No.: 13/262,622

(22) PCT Filed: Apr. 1, 2010

(86) PCT No.: PCT/EP2010/002111
§ 371 (c)(1),
(2), (4) Date: Jan. 26, 2012

(87) PCT Pub. No.: WO2010/115586
PCT Pub. Date: Oct. 14, 2010

(65) Prior Publication Data
US 2012/0135928 A1      May 31, 2012

(30) Foreign Application Priority Data
Apr. 1, 2009   (EP) ..................................... 09157133

(51) Int. Cl.
*A61K 38/24* (2006.01)
*A61P 15/08* (2006.01)
*C07K 1/36* (2006.01)
*C07K 14/59* (2006.01)

(52) U.S. Cl.
CPC ..................... *C07K 14/59* (2013.01)

(58) Field of Classification Search
None
See application file for complete search history.

(56) References Cited

U.S. PATENT DOCUMENTS

| 4,840,896 A | 6/1989 | Reddy et al. |
| 5,021,160 A * | 6/1991 | Wolpert .................. 210/500.35 |
| 5,990,288 A * | 11/1999 | Musick et al. ................ 530/398 |
| 7,132,174 B2 | 11/2006 | Wang et al. |
| 7,157,277 B2 * | 1/2007 | DeFrees et al. ............... 435/351 |
| 2001/0036657 A1 * | 11/2001 | Tang et al. .................... 435/239 |
| 2002/0165366 A1 * | 11/2002 | Musick et al. ................ 530/399 |
| 2003/0059898 A1 | 3/2003 | Beck et al. |
| 2007/0129295 A1 * | 6/2007 | Rossi .............................. 514/12 |
| 2009/0101585 A1 * | 4/2009 | Burg et al. .................... 210/673 |

FOREIGN PATENT DOCUMENTS

| WO | WO 00/63248 | 10/2000 |
| WO | WO 2005/063811 | 7/2005 |
| WO | WO 2006/051070 | 5/2006 |
| WO | WO 2007/065918 | 6/2007 |
| WO | WO 2009/000913 | 12/2008 |

OTHER PUBLICATIONS

Protein and Peptide Purification, 2003, Amersham Biosciences, pp. 1-7.*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Lodish et al (Lodish H, Berk A, Zipursky SL, et al. New York: W. H. Freeman; 2000).*
Graslund et al (Nat Methods. Feb. 2008; 5(2): 135-146).*
Australian IP Office, "Patent Examination Report," mailed in corresponding Australia Patent Application No. 2010234028, dated Nov. 7, 2012, 3 pgs.
Eurasian Patent Organization, "Official Action (English translation only)," mailed in corresponding Eurasian Patent Application No. 201171199, dated Jun. 19, 2013, 3 pgs.
Eurasian Patent Organization, "Official Action (English translation only)," mailed in corresponding Eurasian Patent Application No. 201171199, dated Feb. 28, 2014, 4 pgs.
European Patent Office, "Examination Report," mailed in corresponding Europe Patent Application No. 10 713 424.9, dated Sep. 20, 2013, 4 pgs.
European Patent Office, "Examination Report," mailed in corresponding Europe Patent Application No. 10 713 424.9, dated Jun. 17, 2014, 3 pgs.
Intellectual Property Office of New Zealand, "Examination Report," mailed in corresponding New Zealand Patent Application No. 595661, dated Mar. 26, 2012, 2 pgs.
Israel Patent Office, "Office Action (English translation only)," mailed in corresponding Israel Patent Application No. 215234, dated Jun. 12, 2013, 4 pgs.
Israel Patent Office, "Office Action (English translation only)," mailed in corresponding Israel Patent Application No. 215234, dated Aug. 26, 2014, 3 pg.
Japan Patent Office Name, "Official Action," mailed in corresponding Japan Patent Application No. 20120502514, dated Aug. 12, 2014, 8 pgs.
State Intellectual Property Office of the People's Republic of China, "Official Action (English translation only)," mailed in corresponding China Patent Application No. 201080022681.1, dated Jun. 9, 2013, 8 pgs.

(Continued)

*Primary Examiner* — Brian J Gangle
*Assistant Examiner* — Andrea McCollum
(74) *Attorney, Agent, or Firm* — Hahn Loeser & Parks LLP

(57) ABSTRACT

The present invention relates to a method for purifying a recombinant follicle stimulating hormone (FSH) or recombinant FSH variant. The method comprises the steps of subjecting a liquid containing a recombinant FSH or recombinant FSH variant to an anion exchange chromatography, to a hydrophobic interaction chromatography, and to a dye affinity chromatography, wherein these chromatographies may be performed in any order, and wherein the method neither comprises a weak anion exchange chromatography nor a reverse phase chromatography. The method of purification results in a high yield of recombinant FSH having a desired degree of purity. The obtained FSH is especially useful for the prophylaxis and treatment of disorders and medical indications where FSH preparations are considered as useful remedies.

26 Claims, No Drawings

(56) References Cited

OTHER PUBLICATIONS

State Intellectual Property Office of the People's Republic of China, "Official Action (English translation only)," mailed in corresponding China Patent Application No. 201080022681.1, dated Feb. 20, 2014, 8 pgs.

State Intellectual Property Office of the People's Republic of China, "Official Action (English translation only)," mailed in corresponding China Patent Application No. 201080022681.1, dated Aug. 14, 2014, 7 pgs.

State Intellectual Property Service of Ukraine, "Official Action (English translation only)," mailed in corresponding Ukraine Patent Application No. 2011-12796, dated Jan. 30, 2014, 4 pgs.

* cited by examiner

METHOD FOR PURIFYING RECOMBINANT FSH

CROSS-REFERENCE TO RELATED APPLICATIONS

The present application is a U.S. National Stage entry under 35 U.S.C. §371 of International Application No. PCT/EP2010/002111 filed on Apr. 1, 2010, designating the United States of America and published in English on Oct. 14, 2010, which in turn claims priority to European Patent Application No. 09157133.1 filed on Apr. 1, 2009, each of which is hereby incorporated by reference in its entirety.

The present invention relates to a method for purifying a recombinant follicle stimulating hormone (FSH) or recombinant FSH variant. The method comprises the steps of subjecting a liquid containing a recombinant FSH or recombinant FSH variant to an anion exchange chromatography, to a hydrophobic interaction chromatography, and to a dye affinity chromatography, wherein these chromatography steps may be performed in any order, and wherein the method neither comprises a weak anion exchange chromatography nor a reverse phase chromatography. The method of purification results in a high yield of recombinant FSH having a desired degree of purity. The obtained FSH is especially useful for the prophylaxis and treatment of disorders and medical indications where FSH preparations are considered as useful remedies.

Follicle stimulating hormone (FSH) is produced by the gonadotropic cells of the anterior pituitary and released into the circulation. FSH acts together with the luteinising hormone (LH) in the control of oocyte maturation in females and of spermatogenesis in males. Both FSH and LH belong to a family of heterodimeric glycoproteins which consist of two non-covalently linked α- and β-chains which are encoded by separated genes. Both the α- and β-chains are glycosylated. The α-subunit consists of 92 amino acid residues while the β-subunit consists of 111 amino acid residues, each of which has two potential asparagine-linked glycosylation sites.

Human FSH is used to treat women with unovulation, for stimulation of multifollicular development (superovulation) and in preparation for an assisted conception such as IVF, ICSI, GIFT or CIFT. Furthermore, human FSH is used to stimulate the maturation of follicles in women with low or absent FSH production and to stimulate spermatogenesis in men suffering from oligospermia.

In a typical treatment regimen for ovulation induction, a patient is administered daily injections of FHS or a variant (about 75 to 450 IU FSH/day) for a period of from about 6 to about 12 days. In a typical treatment regimen for controlled ovarian hyperstimulation, a patient is administered daily injections of FSH or a variant (about 150 to 600 IU FSH/day) for a period of from about 6 to about 12 days.

For stimulation of spermatogenesis a regimen using 150 IU FSH three times weekly in combination with 2.500 IU hCG twice weekly has been successful in achieving an improvement in sperm count in men suffering from hypogonadotropic hypogonadism.

Until the 1980s, a primary source of human FSH was urine-derived FSH isolated from urine of childbearing-age women. A further purified form of high-purity, urine-derived FSH was introduced in the 1990s, and finally a recombinant FSH was developed and has been widely used since the year 1998. With the advent of recombinant DNA technology, it became possible to produce human FSH in cell cultures transfected with the nucleic acid sequences coding for the α- and the β-chain. DNA sequences coding for the α- and the β-chains and methods for producing recombinant FSH have been disclosed in e.g. WO 88/10270, WO 86/04589 and EP 0 735 139.

Currently, there are two commercial recombinant human FSH products on the market in Germany, GONAL-f® (follitropin alfa) and Puregon® (follitropin beta), both of which are produced by expression of the DNA sequences coding for the human wild-type α- and β-chains in Chinese Hamster Ovary (CHO) cells.

Because of the importance of FSH in the treatment of fertility disorders, the provision of recombinant FSH of high purity and high specific activity is desirable. FSH treatment requires repeated injections. Highly purified FSH preparations can be administered subcutaneously, permitting self-administration by the patient, thus increasing patient convenience and compliance.

International patent application WO 2006/051070 A1 of Ares Trading S.A. describes a method for purifying recombinant FSH comprising the following steps: 1) dye-affinity chromatography, 2) hydrophobic interaction chromatography; and 3) reverse phase chromatography. Further, WO 2006/051070 A1 discloses a method for purifying FSH comprising the steps of subjecting FSH to 1) anion exchange chromatography, 2) dye affinity chromatography, 3) hydrophobic interaction chromatography, 4) reverse phase chromatography and 5) anion exchange chromatography.

International patent application WO 2005/063811 A1 of Ares Trading S.A. relates to a method for purifying recombinant human FSH comprising the steps of (1) ion exchange chromatography; (2) immobilized metal ion chromatography; and (3) hydrophobic interaction chromatography (HIC).

WO 2007/065918 A2 of Ares Trading S.A. describes a method for purifying FSH comprising the chromatography step: dye affinity chromatography, weak anion exchange chromatography, hydrophobic interaction chromatography, and strong anion exchange chromatography, which may be carried out in any order.

There is an ongoing need for new methods of purifying recombinant FSH and FSH variants. In particular, there is a need for purification methods that avoid the use of reverse phase chromatography steps. Further, it is desirable to have a purification method which does not rely on immunoaffinity chromatography, but may be performed without this cost-intensive step.

According to the present invention, this and further problems are solved by means of the features of the main claim. Advantageous embodiments are defined in the sub-claims.

It is an object of the invention to provide a new, advantageous method for purifying recombinant FSH or a recombinant FSH variant.

In a first aspect, the invention provides a method for purifying recombinant human FSH or an FSH variant starting from a liquid containing the crude FSH, comprising the following steps:
  an anion exchange chromatography,
  a hydrophobic interaction chromatography, and
  a dye affinity chromatography,
which may be performed in any order,
wherein the method avoids any weak anion exchange chromatography as well as any reverse phase chromatography.

In another embodiment, the different chromatographic steps are performed in the following order: (1) anion exchange chromatography, (2) hydrophobic interaction chromatography, and (3) dye affinity chromatography. Anion exchange chromatography (AEC) relies on charge-charge interactions between the proteins in the sample and the charges immobilized on the resin. In anion exchange chromatography, the binding ions of the proteins are negative, and the immobilized functional group is positive. Commonly used anion exchange resins are Q-resin, a quaternary amine, and DEAE resin (DiEthylAminoEthane). However, in general the anion exchange chromatography step can be performed with all common commercially available anion exchange resins or membranes. Anion exchange resins may be used in the form of pre-poured columns. Alternatively, columns may be self-prepared. There are no specific limitations as to the capacity and the geometry of the columns other than the usual ones. The person skilled in the art knows that the amount of anion exchange resin to be used depends on the overall protein content of the cell culture fluid or any other fluid, e.g. the eluate of a preceding chromatography step, applied to the column in the capture step.

Typical strong anion exchange resins that can be used for the purpose of the invention comprise functional groups such as: quaternary aminoethyl (QAE) moieties, resins include e.g. TOYOPEARL QAE (available from Tosoh Bioscience, Germany), SELECTACEL QAE (a quaternary aminoethyl derivative of cellulose, available from Polysciences Inc., Pennsylvania USA) and others; quaternary ammonium (Q) moieties, resins include e.g. Q SEPHAROSE XL, Q SEPHAROSE FF, Q SEPHAROSE HP (available from GE Healthcare, Germany), RESOURCE Q (available from GE Healthcare, Germany), MACRO PREP HIGH Q (Bio-Rad, California, USA), TOYOPEARL Super Q (available from Tosoh Bioscience, Germany), UNOSPHERE Q (available from Bio-Rad, California, USA), and trimethylammoniumethyl (TMAE) groups, resins include e.g. FRACTOGEL EMD TMAE (available from Merck, Germany).

The anion exchange chromatography is preferably a strong anion exchange chromatography which is performed using a strong anion exchange resin having—$N^+(CH_3)_3$ functional groups, or a resin having similar characteristics.

Preferred examples of strong anion exchange resins which can be used for the purpose of the invention are quaternary ammonium strong anion exchanger resins known in the art as UNOSPHERE Q, Q SEPHAROSE HP and other resins having quaternary ammonium (Q) moieties.

The characteristics of the strong anion exchanger UNOSPHERE Q are as follows:

| | |
|---|---|
| Functional group | —$N^+(CH_3)_3$ |
| Total ionic capacity | 120 µeq/ml |
| Dynamic binding capacity | |
| 150 cm/hr | 180 mg/ml |
| 600 cm/hr | 125 mg/ml |
| Shipping counter ion | Cl$^-$ |
| Median particle size | 120 µm |
| Recommended linear flow rate range | 50-1200 cm/hr |
| Chemical stability | |
| 1.0M NaOH (20° C.) | up to 2,000 hrs |
| 1.0M HCl (20° C.) | up to 200 hrs |
| Volume changes | |
| pH 4-10 | <5% |
| 0.01-1.0M NaCl | <5% |
| pH stability | 1-14 |

The characteristics of the strong anion exchanger Q SEPHAROSE HP are as follows:

| | |
|---|---|
| Ionic capacity | 0.14-0.20 mmol Cl$^-$/ml |
| Dynamic capacity | 70 mg BSA/ml medium |
| Rec. flow velocity | 30-150 cm/h |
| Max. pressure over the Packed bed during operation | 3 bar (42 psi, 0.3 MPa) |
| HiLoad column hardware pressure limit | 5 bar (73 psi, 0.5 MPa) |
| Average particle size | 34 µm |
| Exclusion limit ($M_r$) | approx. $4 \times 10^6$ globular protein |
| Matrix | cross-linked agarose, 6% |
| pH stability | 2-12 (working and long term), 1-14 (short term) |
| Chemical stability | stable in all commonly used buffers |

It is preferable to avoid the use of weak anion exchange resins, such as those based on diethylaminoethyl (DEAE) or dimethylaminoethyl (DMAE) as the functional groups.

The step of anion exchange chromatography is preferably carried out using a buffer having a mildly alkaline pH, e.g. at or about 7.0 to at or about 9.0, or at or about 7.5 to at or about 8.5. Suitable buffers include, for example, borate buffer, triethanolamine/iminodiacetic acid Tris, ammonium acetate, tricine, bicine, TES, HEPES, TAPS. The use of a Tris buffer is preferred. Elution from the anion exchange resin is usually achieved by increasing the conductivity of the mobile phase through the addition of salt, preferably sodium chloride.

The hydrophobic interaction chromatography (HIC) of the method of the invention can be performed using a HIC resin having a relatively mildly hydrophobic surface (compared to the much stronger hydrophobic surface of a reverse phase resin). Proteins with hydrophobic surface properties are attracted to such resins which commonly have ether, phenyl, butyl or hexyl groups.

The HIC can be performed with all common commercially available HIC resins. HIC resins that can be used for the purpose of the invention comprise matrices such as Butyl, Phenyl, Propyl or Octyl SEPHAROSE, SOURCE 15 (all available from GE Healthcare, Germany), Macro-Prep Methyl or t-butyl HIC support (Bio-Rad, Germany) or FRACTOGEL EMD with propyl or phenyl ligands (Merck AG, Germany), TOYOPEARL HIC resins, such as TOYOPEARL Butyl 650 M and similar HIC resins (Tosoh Bioscience).

In a preferred embodiment, the hydrophobic interaction chromatography is performed using a resin consisting of cross-linked agarose beads derivatized with phenyl, butyl or octyl groups, or a resin having similar characteristics. The characteristics of Phenyl SEPHAROSE 6 FF (available from GE Healthcare) are given below.

| | |
|---|---|
| Ligand density | |
| Phenyl Sepharose ™ 6 Fast Flow (low sub) | 25 µmol/ml medium |
| Phenyl Sepharose ™ 6 Fast Flow (high sub) | 40 µmol/ml medium |
| Binding capacity | |
| Phenyl Sepharose ™ 6 Fast Flow (low sub) | 10 mg IgG/ml medium 24 mg HSA/ml medium |
| Phenyl Sepharose ™ 6 Fast Flow (high sub) | 30 mg IgG/ml medium 36 mg HSA/ml medium |
| Pressure/flow spec. | 200-400 cm/h, 1 bar XK 50/60 column, bed height 25 cm |
| pH stability | 2-14 (short term), 3-13 (long term) |
| Chemical stability | Stable in common buffers, chaotropic agents, detergents, and polar organic solvents. |
| Average particle size | 90 µm |
| Storage | 20% ethanol |
| Storage temperature | 4° C. to 30° C. |

Binding on the HIC resin is achieved in a buffer with a high conductivity, obtained through the addition of salt (NaCl, ($NH_4$)$_2SO_4$ or $Na_2SO_4$ for example). Elution in the HIC step is usually carried out by reducing the conductivity of the mobile phase (i.e. reducing the salt concentration), using a buffer having a pH at or about 5 to at or about 9, more preferably at or about 6 to at or about 8, most preferably at or about 7 to at or about 8.

Equilibration, washing and elution buffers may comprise all buffer types usually used for HIC. Thus, buffering agents comprise sodium phosphate, sodium acetate, Tris/HCl, HEPES, or other buffering agents. Moreover, buffers may contain between 0.5 mM and 3 M NaCl, KCl or other suitable salts depending on whether the buffer is used for equilibration, washing or elution. Equilibration and washing buffers contain higher concentrations of the aforementioned salts than elution buffers.

A particularly preferred buffer in the HIC step is a Tris/HCl buffer containing sodium chloride.

The dye affinity chromatography of the method of the invention can be performed using a resin having as an immobilised ligand a dye compound which is well known to a person skilled in the art, i.e. CIBACRON Blue F3G-A (1-amino-4-[4-[[4-chloro-6-(2-sulfoanilino)-1,3,5-triazin-2-yl]amino]-3-sulfoanilino]-9,10-dioxoanthracene-2-sulfonic acid). The term "immobilized" is well understood by a person skilled in the art and means that the ligand is derivatized in the sense that it is chemically linked to the resin.

In a preferred embodiment, the dye affinity chromatography is performed with CIBACRON Blue F3G-A (1-amino-4-[4-[[4-chloro-6-(2-sulfoanilino)-1,3,5-triazin-2-yl]amino]-3-sulfoanilino]-9,10-dioxoanthracene-2-sulfonic acid) as the ligand, covalently coupled to any matrix, e.g. an agarose matrix. Preferably, the dye affinity chromatography is performed using the resin known as Blue SEPHAROSE FF (available from GE Healthcare, Germany). The technical characteristics of Blue SEPHAROSE FF are given below:

| | |
|---|---|
| Ligand | CIBACRON Blue F3G-A (1-amino -4-[4-[[4-chloro-6-(2-sulfoanilino)-1,3,5-triazin-2-yl]amino]-3-sulfoanilino]-9,10-dioxoanthracene-2-sulfonic acid) |
| Ligand coupling method | Triazine coupling |
| Binding capacity | >18 mg human serum albumin/ml medium |
| Ligand density | ≈7 μmol CIBACRON Blue (1-amino -4-[4-[[4-chloro-6-(2-sulfoanilino)-1,3,5-triazin-2-yl]amino]-3-sulfoanilino]-9,10-dioxoanthracene-2-sulfonic acid)/ml medium |
| Matrix | Highly cross-linked agarose, 6% |
| Average particle size | 90 μm |
| pH stability | 4-12 (long term), 3-13 (short term) |
| Storage | 20% ethanol, 0.1M potassium phosphate buffer, pH 8.0 |
| Storage temperature | 4° C. to 30° C. |
| Chemical stability | 40° C. for 7 days in: 70% ethanol, 6M guanidine hydrochloride, 8M urea |

It is understood that the dye affinity chromatography of the method of the invention may be performed with alternative resins, having similar characteristics. Examples of alternative resins include: TOYOPEARL AF-blue-HC-650M (Tosoh Biosciences), Blue CELLTHRU BigBead (Sterogene), SWELLGEL Blue (Pierce), CIBACHROME blue 3GA-agarose 100 (Sigma), AFFI-GEL Blue (Bio-Rad), ECONO-PAC blue cartridges (Bio-Rad), CIBACRON Blue 3GA (Sigma).

Elution in the step of immobilized dye affinity chromatography is preferably carried out using a Tris/HCl buffer or a phosphate buffer. Most preferred is a Tris/HCl buffer containing sodium chloride. The pH of the eluent is preferably at or about 7 to at or about 9, most preferably the pH is in the range between 7 and 8.

In another aspect, the method of purifying a recombinant FSH or FSH variant according to the invention comprises the steps of subjecting a liquid containing said FSH or FSH variant to
an anion exchange chromatography,
a hydrophobic interaction chromatography,
a dye affinity chromatography, and
further to a cation exchange chromatography
which may be performed in any order,
wherein the method avoids any weak anion exchange chromatography as well as any reverse phase chromatography.

In one embodiment the steps are performed in the following order: (1) anion exchange chromatography, (2) hydrophobic interaction chromatography, (3) dye affinity chromatography, and (4) cation exchange chromatography.

Cation exchange chromatography (CEC) relies on charge-charge interactions between the proteins in the sample and the charges immobilized on the resin. In cation exchange chromatography, the binding ions of the proteins are positive and the immobilized functional group is negative. Commonly used cation exchange resins are S-resin, sulfate derivates, and CM (carboxymethyl) resins, carboxylated derived ions.

However, in general the cation exchange chromatography step can be performed with all common commercially available cation exchange resins or membranes. Cation exchange resins may be used in the form of pre-poured columns or membranes on which the functional group, e.g. sulfonic acid, is fixed. Alternatively columns may be self-prepared. There are no specific limitations as to the capacity and the geometry of the columns other than the usual ones. The person skilled in the art knows that the amount of cation exchange resin to be used depends on the overall protein content of the cell culture fluid or any other fluid, e.g. the eluate of a preceding chromatography step.

Typical cation exchange resins that can be used for the purpose of the invention are available from GE Healthcare and other manufactures of ion chromatography accessories and columns. Commonly, CEC is performed using buffers at pH values between 4 and 7.

In a preferred embodiment, the cation exchange step of the method of the invention is performed as a membrane cation exchange. Preferably, the cation exchange step is carried out with a strong acidic cation exchanger sulfonic acid fixed on a membrane or an exchanger having similar characteristics.

Suitable membrane adsorbers for use in the cation exchange step of the invention are known in the art and available from several suppliers. For example, the cation exchange chromatography of the method of the invention can be performed using a membrane made from regenerated cellulose and having a chromatographic matrix of sulfonic acid formed on the cellulose backbone. An example of a useful membrane adsorber are the SARTOBIND S membrane Adsorbers sold by Sartorius. The technical data of the SARTOBIND S membrane Adsorbers are given below.

| | |
|---|---|
| Designation | Sartobind SingleSep ® (strong acid cation exchanger S) |
| Ligand | sulfonic acid (R—$CH_2$—$SO_3^-$) |
| Static binding capacity | ≥0.8 mg/cm² (29 mg/ml) measured with bovine serum albumin and hen egg lysozyme |
| Ion capacity | 4-6 μeq/cm² |

Membrane

| | |
|---|---|
| Base Material | stabilized reinforced cellulose |
| Membrane thickness | 275 μm |
| Nominal pore size | >3 μm |

Capsule

| | |
|---|---|
| Design | Cylindrical, nominal number of layers: 15 |
| Bed height: | 4 mm |
| Material Capsule | Polypropylene (FDA) |
| Max. pressure | 0.4 MPa (4 bar, 58 psi) |
| pH stability | 3-14 (short term) |
| Storage | discard after one use |
| Chemical stability | Stable against all commonly used buffers in chromatography, 1M NaOH (30-60 min at 20° C.), 8M urea, 8M guanidine hydrochloride, ethanol, acetone, and 100% acetonitrile. Avoid oxidizing agents. |

The CEC step can be performed according to the manufacturer's protocol. For example, a Tris-HCl buffer can be used at pH 7.0.

It was found that the CEC step, preferably the cation membrane adsorber step, clears host cell proteins of all molecular sizes whilst keeping process times short. The yield, at about 95%, is very favourable because FSH does not bind to the adsorber at pH 7.0.

In general, it was found that cation exchange chromatography in the form of a chromatographic membrane is very useful for the purification of recombinant FSH or FSH variant. Thus, in another aspect, the invention relates to the use of a cation membrane adsorber in a method of purifying FSH or FSH variant. In a preferred embodiment, the cation membrane adsorber is a cation exchanger adsorber, preferably a strong cation exchange adsorber, made from regenerated cellulose and having a chromatographic matrix of sulfonic acid formed on the cellulose backbone.

In another aspect, the method of purifying a recombinant FSH or FSH variant according to the invention comprises the steps of subjecting a liquid containing said FSH or FSH variant to
  an anion exchange chromatography,
  a hydrophobic interaction chromatography,
  a dye affinity chromatography,
  an optional cationic exchange chromatography, and
further to an additional anion exchange chromatography,
which may be performed in any order,
wherein the method avoids any weak anion exchange chromatography as well as any reverse phase chromatography.

In one embodiment the steps are performed in the following order: a first anion exchange chromatography, a hydrophobic interaction chromatography, a dye affinity chromatography, an optional cation exchange chromatography, and a second anion exchange chromatography.

The second anion exchange chromatography can be performed using typical anion exchange resins as mentioned above in connection with the first anion exchange chromatography. Also the second anion exchange chromatography is preferably a strong anion exchange chromatography which is performed using a strong anion exchange resin having —N$^+$(CH$_3$)$_3$ functional groups, or a resin having similar characteristics. Preferred examples of strong anion exchange resins which can be used for the purpose of the invention are quaternary ammonium strong anion exchanger resins known in the art as UNOSPHERE Q, Q SEPHAROSE HP and other resins having quaternary ammonium (Q) moieties. The characteristics of the strong anion exchanger UNOSPHERE Q and Q SEPHAROSE HP are given above in connection with the first anion exchange chromatography. Also in the second anion exchange chromatography step it is preferable to avoid the use of weak anion exchange resins, such as those based on diethylaminoethyl (DEAE) or dimethylaminoethyl (DMAE) as the functional groups.

The step of anion exchange chromatography is preferably carried out using a buffer having a mildly alkaline pH, e.g. at or about 7.0 to at or about 9.0, or at or about 7.5 to at or about 8.5. Suitable buffers include, for example, borate buffer, triethanolamine/iminodiacetic acid Tris, ammonium acetate, tricine, bicine, TES, HEPES, TAPS. The use of a Tris buffer is preferred. Elution from the anion exchange resin is usually achieved by increasing the conductivity of the mobile phase through the addition of salt, preferably sodium chloride.

In one embodiment, the second anion exchange chromatography is performed using a Tris-HCl/sodium chloride buffer as eluent at a pH in the range between 7.0 and 9.0.

In another aspect, the method of purifying a recombinant FSH or FSH variant according to the invention comprises the steps of subjecting a liquid containing said FSH or FSH variant to
  an anion exchange chromatography,
  a hydrophobic interaction chromatography, and
  a dye affinity chromatography,
which may be performed in any order,
wherein the method avoids any weak anion exchange chromatography as well as any reverse phase chromatography, and
wherein the method further comprises a size exclusion chromatography.

In another aspect, the method of purifying a recombinant FSH or FSH variant according to the invention comprises the steps of subjecting a liquid containing said FSH or FSH variant to
  an anion exchange chromatography,
  a hydrophobic interaction chromatography,
  a dye affinity chromatography,
  an optional cationic exchange chromatography,
  an optional further anion exchange chromatography, and
  a size exclusion chromatography,
which may be performed in any order,
wherein the method avoids any weak anion exchange chromatography as well as any reverse phase chromatography.

In one embodiment the steps are performed in the following order: an anion exchange chromatography, a hydrophobic interaction chromatography, a dye affinity chromatography, an optional cation exchange chromatography, an optional further anion exchange chromatography, and a size exclusion chromatography.

In a preferred embodiment, the method of the invention comprises the following steps in the following order: a first anion exchange chromatography, a hydrophobic interaction chromatography, a dye affinity chromatography, an optional cation exchange chromatography, an optional second anion exchange chromatography, and a size exclusion chromatography.

Size exclusion chromatography (SEC), also known as gel filtration chromatography, is a chromatographic method in which particles, e.g. proteins and other biomolecules, are separated based on their size. A typical gel medium for SEC is polyacrylamide, dextran, agarose or a mixture thereof. SEC matrixes are available from various manufacturers of chromatographic accessories and column, e.g. from Tosoh Bioscience LLC or GE Healthcare.

The size exclusion chromatography is preferably performed using a matrix of spherical composite of cross-linked agarose and dextran.

Examples of useful size exclusion chromatography matrices are matrices known in the art as SUPERDEX 75 pg, available for example from GE Healthcare. SUPERDEX 75 pg columns allow for high-resolution separation of proteins, peptides, and other biomolecules according to size. Generally, size exclusion columns are ideal for the polishing step in a purification procedure.

The technical details of the SUPERDEX 75 pg matrix are as follows:

| | |
|---|---|
| Exclusion limit ($M_r$) | $1 \times 10^5$ globular protein |
| Separation range ($M_r$) | 3000-70 000 globular protein |
| Matrix | Spherical composite of cross-linked agarose and dextran |
| Average particle size | 34 μm |
| Chemical stability | Stable in all common buffers: 1M acetic acid, 8M urea, 6M guanidine hydrochloride, 30% isopropyl alcohol, 70% ethanol, 1M NaOH (for cleaning in place) |
| pH stability | 3-12 (working and long term), 1-14 (short term) |

Superdex™ 10/300 GL Colum ns (Tricorn)*

| | |
|---|---|
| Bed dimensions | 10 × 300 mm |
| Recommended sample volume | 25-250 μl |
| Bed volume | 24 ml |
| Max. pressure | 18 bar (261 psi, 1.8 MPa) |
| Max. flow rate ($H_2O$ at 25° C.) | 1.5 ml/min |
| Theoretical plates | >30 000 $m^{-1}$ |

Superdex™ PC 3.2/30 Columns

| | |
|---|---|
| Bed dimensions | 3.2 × 300 mm |
| Bed volume | 2.4 ml |
| Recommended sample volume | 2-25 μl |
| Max. pressure | 24 bar (348 psi, 2.4 MPa) |
| Max. flow rate ($H_2O$ at 25° C.) | 0.100 ml/min |
| Theoretical Plates | >30 000 $m^{-1}$ |
| Storage | 20% ethanol |
| Storage temperature | 4° C. to 30° C. |

The SEC step can be performed according to the manufacturer's protocol. For example, a sodium phosphate buffer can be used at pH 6 to 8, preferably at about pH 7.0.

In a preferred embodiment of the invention, the method of the invention comprises the following steps in the following order: a first anion exchange chromatography, a hydrophobic interaction chromatography, a dye affinity chromatography, a cation exchange chromatography, a second anion exchange chromatography, and a size exclusion chromatography.

In a preferred embodiment, the cation exchange chromatography step of the method of the invention is performed as a membrane cation exchange. Preferably, the cation exchange step is carried out with a strong acidic cation exchanger sulfonic acid, fixed on a membrane or an exchanger having similar characteristics.

Further, the method of the invention comprises one or more ultrafiltration and/or nanofiltration steps. Ultrafiltration is a form of membrane filtration in which hydrostatic pressure forces a liquid against a semipermeable membrane. Suspended solids and solutes of high molecular weight are retained, while water and low molecular weight solutes pass through the membrane. Ultrafiltration is a commonly used method of separation for purifying and concentrating macromolecular solutions, especially protein solutions. Ultrafiltration is similar to nanofiltration, however differing in terms of the size of the molecules it retains. In the framework of the present invention, a molecular weight cut off of 10 kDa is preferred (10 kDa UF). UF membranes may also be used for diafiltration to remove salts and other microspecies from solution via repeated or continuous dilution and reconcentration.

In a preferred embodiment of the invention, the process of purification comprises one or more ultrafiltration/diafiltration and/or nanofiltration steps. These filtration steps can be performed using commercially available filtration devices, e.g. available from GE Healthcare or Sartorius.

The ultrafiltration is preferably performed using the SARTOCON cassettes and SARTOCON Slice cassettes sold by Sartorius.

| | |
|---|---|
| Membrane | Polyethersulfone (PESU) or Hydrosart ® |
| Molecular weight cut-off | 10 kD |
| Filter area | 0.02 to 0.7 $m^2$ |
| Feed pressure | 4 bar (58 psi) maximum |
| pH stability | 1-14 |
| Operating temperature | 50° C. maximum, at 20° C. |
| Cleaning | 1M NaOH, 40° C. |
| Disinfection | 1M NaOH, 40-50° C., 30 min |
| Storage | 0.1M NaOH |

The polyethersulfone membrane (PESU) used in the cross-flow cassettes sold by Sartorius is a stable membrane polymer that features a broad pH and temperature range.

The Hydrosart ultrafiltration cassettes sold by Sartorius can also be used. HYDROSART is a stabilized cellulose based membrane that has been optimized for biotechnological applications. The HYDROSART ultrafiltration membranes and cassettes are available in the following nominal molecular weight cutoffs: 2 kD, 5 kD, 10 kD and 30 kD.

In a preferred embodiment, the method of purification includes a nanofiltration step. The nanofiltration can be performed using any useful nano-filter device. The nanofiltration is preferably performed using PLANOVA filters, available from Asahi Kasei Medical Co., Ltd.

PLANOVA filters are designed to remove viruses during the manufacture of biotherapeutic drug products such as biopharmaceuticals. They are based on a hollow-fiber microporous membrane constructed of naturally hydrophilic cuprammonium regenerated cellulose with a narrow pore distribution, PLANOVA filters are available as single-use, self-contained modules in four mean pore sizes of 15 nm, 19 nm, 35 nm, and 72 nm (PLANOVA 15N, 20N, 35N, and 75N, respectively). In the process of the invention it is preferred to use a PLANOVA 15N filter, i.e. a filter having a mean pore size of 15 nm. The filter is used in accordance with the supplier's protocol.

It is preferred that the method of purifying FSH according to the invention does not comprise a metal ion affinity chromatography.

Further, it is also preferred that the method of the invention avoids an immunoaffinity chromatography. The purification of FSH without immunoaffinity chromatography steps eliminates possible resulting interference of impurities or infectious agents, derived from the preparation of the antibody, with the FSH compound.

In another embodiment, the invention relates to a method of purifying a recombinant FSH or recombinant FSH variant, comprising the step of subjecting a liquid containing said FSH or FSH variant to a membrane cation exchanger.

In a preferred embodiment, the membrane cation exchanger is a strong acidic cation exchanger sulfonic acid, fixed on a membrane, or an exchanger having similar characteristics.

Suitable membrane adsorbers for use in the method of the invention are known in the art and available from several suppliers. For example, the cation exchange chromatography of the method of the invention can be performed using a membrane made from regenerated cellulose and having a chromatographic matrix of sulfonic acid formed on the cellulose backbone. An example of a useful membrane adsorber are the SARTOBIND S membrane Adsorbers sold by Sartorius. The technical details thereof are given above.

In another embodiment, the method of purifying a recombinant FSH or recombinant FSH variant comprising the step of subjecting a liquid containing FSH to a membrane cation exchanger further comprises a hydrophobic interaction chromatography.

The hydrophobic interaction chromatography of the method of the invention can be performed as described above in connection with the method of purifying a recombinant FSH or recombinant FSH variant, comprising the steps of subjecting a liquid containing said FSH or FSH variant to an anion exchange chromatography, a hydrophobic interaction chromatography, and a dye affinity chromatography, which are performed in any order,
wherein the method neither comprises a weak anion exchange chromatography nor a reverse phase chromatography, and preferred embodiments thereof.

In a preferred embodiment, the hydrophobic interaction chromatography is performed using a resin consisting of cross-linked agarose beads derivatized with phenyl or butyl groups, or a resin having similar characteristics.

Unless otherwise indicated, the following definitions are intended to illustrate and define the meaning and scope of the various terms used to describe the present invention.

The term "FSH" refers to a follicle-stimulating hormone polypeptide as a full-length mature protein which includes, but is not limited to, human FSH or "hFSH", whether produced recombinantly or isolated from human sources, such as the urine of post-menopausal women. The protein sequence of the human glycoprotein and the protein sequence of the human FSH β-subunit are known to the skilled person from the scientific and patent literature (see e.g. WO 2004/087213).

The amino acid sequence of the α-chain of human FSH is depicted in SEQ ID No. 1, and the amino acid sequence of the β-chain of human FSH is depicted in SEQ ID No. 2 as attached to this specification. These amino acid sequences correspond to the wild-type amino acid sequences of the α- and the β-chain of human FSH as deposited under accession number J 00152 in the EMBL database and under accession number NM 000510 in the NCBI database, respectively.

The wild-type nucleic acid sequences coding for human FSH are shown in SEQ ID No. 3 (=α-chain) and No. 4 (=β-chain).

The recombinant FSH may be encoded by the wild-type nucleic acid sequence as naturally found in humans, or it may be encoded by an altered nucleic acid sequence whose expression results in an FSH having the wild-type amino acid sequence, i.e. the wild-type protein sequence as naturally found in humans.

The nucleic acid sequence coding for human FSH can, for example, be altered in such a way that one or both of the nucleic acid sequences which code for the α- and the β-chain of human FSH have been adapted to the codon usage in Chinese Hamster Ovary (CHO) cells in order to increase the expression level and yield of recombinant FSH in these host cells.

An example of nucleic acid sequences which code for human FSH and which have been modified with regard to the codon usage in CHO cells is described in the international patent application WO 2009/000913. The modified nucleic acid sequence coding for the β-chain of human FSH is the coding region of the nucleic acid sequence depicted in SEQ ID No. 5 (in SEQ ID No. 5 the coding region starts at nucleotide 56 and extends up to nucleotide 442), and the modified nucleic acid sequence coding for the α-chain of human FSH is the coding region of the nucleic acid sequence given in SEQ ID No. 6 (in SEQ ID No. 6 the coding region starts at nucleotide 19 and extends up to nucleotide 366). A CHO cell line containing a recombinant nucleic acid molecule comprising a first modified nucleic acid sequence coding for the β-chain of human FSH and a second modified nucleic acid sequence coding for the α-chain of human FSH was deposited on 28 Mar. 2007 at the DSMZ in Braunschweig under deposit number DSM ACC2833.

In a preferred embodiment, the FSH liquid formulation according to the present invention contains a recombinant human wild-type FSH which is obtained by recombinant gene expression from FSH nucleic acid sequences which are modified with regard to codon usage in CHO cells with respect to both the β-chain of human FSH and the α-chain of FSH. In another preferred embodiment, the recombinant FSH is obtained by expression from the FSH nucleic acid sequences disclosed in WO 2009/000913.

The expression "FSH variant" is meant to encompass those molecules differing in amino acid sequence, glycosylation pattern or in inter-subunit linkage from human FSH but exhibiting FSH activity. Examples include CTP-FSH, a long-acting modified recombinant FSH, consisting of the wild-type α-subunit and a hybrid β-subunit in which the carboxy terminal peptide of hCG has been fused to the C-terminal of the β-subunit of FSH, as described in LaPolt et al. (1992) Endocrinology, 131, 2514-2520; or Klein et al. (2003) Human Reprod., 18, 50-56. Also included is a single-chain CTP-FSH, a single-chain molecule described by Klein et al. (2002) Fertility & Sterility, 77, 1248-1255. Other examples of FSH variants include FSH molecules having additional glycosylation sites incorporated into the α- and/or β-subunit, as disclosed in WO 01/58493, and FSH molecules with inter-subunit S—S bonds, as disclosed in WO 98/58957. Other examples of FSH variants are disclosed in WO 2004/087213, which are characterized by carboxy terminal deletions of the β-subunit. Other examples of FSH variants include FSH molecules having an altered degree of glycosylation compared to wild-type FSH due to changes in the amino acid sequence of the protein by which additional glycosylation site(s) are introduced or naturally occurring glycosylation site(s) are deleted.

Further, the FSH or FSH variant according to the invention can be an FSH molecule which has been modified by chemical moieties. Such FSH conjugates can for example comprise poly alkylen glycol (such as PEG), hydroxyalkyl starch (such as HES) or other polymeric moieties.

FSH heterodimers or FSH variant heterodimers can be produced by any suitable method, such as recombinantly, by isolation or purification from natural sources or by chemical synthesis, or any combination thereof.

The use of the term "recombinant" refers to preparations of FSH or FSH variants that are produced through the use of recombinant DNA technology (see for example WO 85/01958). The sequences for genomic and cDNA clones of FSH are known for the α- and β-subunits of several species. Various methods of producing recombinant FSH or FSH variants using recombinant technology are described in the prior art, see for example European patent application EP 0 711 894 and European patent application EP 0 487 512.

Preferably, the FSH purified according to the invention has an alpha subunit according to SEQ ID No. 1 and a beta subunit according to SEQ ID No. 2.

In another aspect, the invention relates to a purified FSH or FSH variant protein obtained by the method of purification according to the invention.

The invention further relates to a pharmaceutical composition comprising the FSH or FSH variant purified using the method of the invention as well as a pharmaceutically acceptable excipient. In a preferred embodiment, the pharmaceutical composition contains a preservative and can be used for multi-dose administration. Preferred pharmaceutical compositions are described in PCT/EP2009/051451.

Further, the invention also relates to the use of the FSH or FSH variant purified using the method of the invention, or to the use of a pharmaceutical composition comprising said FSH or FSH variant in combination with pharmaceutically acceptable excipients for the treatment of fertility disorders.

The recombinant human FSH is purified from the host cell culture supernatant by the method of the invention. The recombinant human FSH or FSH variant is preferably produced as described in the international patent application WO 2009/000913.

Most preferably, the FSH is human FSH which has been produced recombinantly, particularly preferably produced in Chinese Hamster Ovary cells transfected with a vector or vectors comprising DNA coding for the human glycoprotein α-subunit and the β-subunit of FSH, either encoded by SEQ ID No. 3 and 4 (=wild-type nucleic acid sequences) or by SEQ ID No. 5 and 6 (=codon-optimized nucleic acid sequences). DNA encoding the α- and β-subunits may be present on the same or different vectors.

Recombinant FSH has several advantages over its urinary counterpart. Culture and isolation techniques using recombinant cells permit consistency between batches. In contrast, urinary FSH varies greatly from batch to batch in such characteristics as purity, glycosylation pattern, sialylation and oxidation of the subunits. Due to greater batch-to-batch consistency and purity of recombinant FSH, the hormone can be readily identified and quantified using techniques such as isoelectric focussing (IEF). The ease with which recombinant FSH can be identified and quantified permits the filling of vials by mass of hormone (fill-by-mass) rather than filling by bioassay.

The term "FSH activity" refers to the ability of an FSH formulation to elicit biological responses associated with FSH, such as ovarian weight gain in the Steelman-Pohley assay (Steelman et al. (1953) Endocrinology 53, 604-616), or follicular growth in a female patient. Follicular growth in a female patient can be evaluated by ultrasound, for example, in terms of the number of follicles having a mean diameter of about 16 mm on day 8 of stimulation. Biological activity is evaluated with respect to an accepted standard for FSH.

The specific in vivo bioactivity of the recombinant FSH is usually in the range of about 8,000 IU FSH/mg of protein to about 16,000 IU FSH/mg of protein. For example, the recombinant human FSH in the commercially available product PUREGON (follitropin beta) (from Organon) has a specific bioactivity of about 10,000 IE/mg protein, and for GONAL-F (follitropin alfa) from Serono the bioactivity of the recombinant human FSH is about 13,600 IE/mg protein.

The FSH activity may be determined by known methods relating to FSH and other gonadotrophins. Such methods include e.g. enzyme immunoactivity assay (EIA) or reporter gene assays. The bioactivity is usually determined by the bioassay described in the European Pharmacopoeia, 5th Edition for urine derived FSH, the bioactivity being estimated by comparing the effect of FSH in enlarging the ovaries of immature rats treated with chorionic gonadotrophin with the same effect of a Standard Preparation.

The biological activity of the FSH or FSH variant can be assessed by comparing, under given conditions, its effect in enlarging the ovaries of immature rats treated with chorionic gonadotrophin with the same effect using an International Standard preparation or of a reference preparation calibrated in International Units (European Pharmacopoeia, 5$^{th}$ Edition).

The measurement of FSH activity in vitro is e.g. described by Albanese et. al. (1994) Mol. Cell. Endocrinol. 101:211-219.

The purity of the FSH or FSH variant obtained by the method of the invention is at least 95%, preferably at least 97%, more preferably at least 99% and most preferably more than 99%. The degree of purity can be determined by means of HPLC analysis. Suitable materials and protocols for conducting such analysis can be obtained from commercial suppliers such as Vydac or TOSOH Bioscience.

The following examples are provided merely to further illustrate the method of purification of the invention. The scope of the invention shall not be construed as merely consisting of the following examples.

EXAMPLES

Example 1

Preparation of a Recombinant Human FSH by Recombinant Technologies

Recombinant human FSH is produced in transfected CHO host cells by standard methods. These methods include the generation of a CHO cell clone which produces recombinant human FSH from one or more recombinant nucleic acid molecules which code for the α-chain and the β-chain of human FSH, and cultivation of the host cells under suitable conditions. The recombinant human FSH is then purified from the cell culture according to the invention.

In a preferred embodiment, the recombinant human FSH is produced as described in international patent application WO 2009/000913.

Example 2

Purification of FSH from Cell Culture

The purification scheme is as follows:

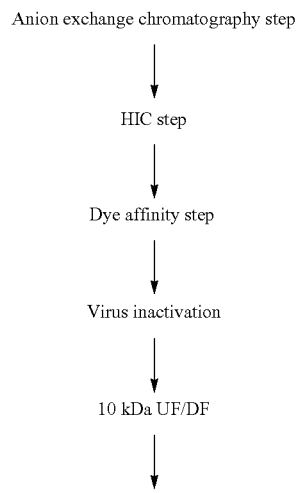

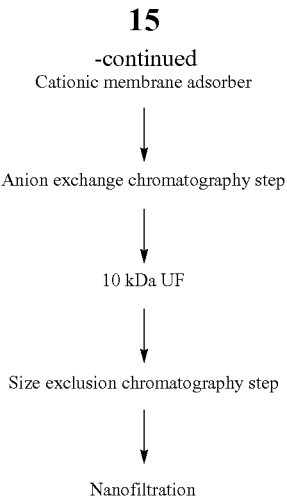

Cationic membrane adsorber

↓

Anion exchange chromatography step

↓

10 kDa UF

↓

Size exclusion chromatography step

↓

Nanofiltration

The fermentation duration was 28 days, and the fermentation volume was 30 L. The harvest was 0.22 nm filtered and diluted with RO water by factor 3.5.

Anion exchange chromatography (AEC) step:

The diluted cell culture supernatant harvest was applied to anion exchange chromatography using the quaternary ammonium strong anion exchanger resin known in the art as UNOSPHERE Q. This matrix is available from BioRad.

Three column volumes (CV) of 50 mM Tris-HCl, pH 7.6 were used for equilibration. The column was loaded with the harvest (diluted 1:3.5 with RO water; the harvest titer was approx. 1.8 ng FSH/mL) and post-washed with 50 mM Tris-HCl, pH 7.6 (5 CV). Then the column was washed with 50 mM Tris-HCl, 15 mM NaCl, pH 7.6 (5 CV), and the protein was eluted using 50 mM Tris-HCl, 200 mM NaCl, pH 7.6 (8 CV). The step yield was 90% and higher.

HIC Step:

The HIC was carried out using a resin consisting of cross-linked agarose beads derivatized with phenyl. Phenyl SEPHAROSE 6 FF (available from GE Healthcare) is a highly cross-linked deviated based on agarose. It is physically and chemically stable allowing high flow rates and increased resin lifetimes. The technical details of this resin are given above.

Eight AEC eluates were pooled and diluted with 50 mM Tris-HCl, 4.5 NaCl, pH 7.6 by factor 3. The HIC column was equilibrated with 50 mM Tris-HCl, 3 M NaCl, pH 7.6 (4 CV) and loaded with the 1:3 diluted AEC eluate. Then the column was post-washed using 50 mM Tris-HCl, 3 M NaCl, pH 7.6 (3 CV) and washed using 50 mM Tris-HCl, 1.8 M NaCl, pH 7.6 (5 CV). The wash buffer with 1.8 M NaCl was found to have a good clearance potential without detectable FSH loss. The protein was then eluted with 50 mM Tris-HCl, 0.8 M NaCl, pH 7.6 (6 CV).

The FSH yield of the HIC step was >95% without any significant loss during load and a good total protein clearance potential of approx. factor 10. These data show that the developed HIC step is a very efficient purification step with reasonable yield and product quality.

Dye Affinity Chromatography Step:

Blue SEPHAROSE FF, available from GE Healthcare, was used for the dye affinity chromatography step. The HIC eluate was diluted with 50 mM Tris-HCl, pH 7.6 by factor 4. The column was equilibrated using 50 mM Tris-HCl, pH 7.6 (3 CV) and loaded with the 1:4 diluted HIC eluate. The column was post-washed with 50 mM Tris-HCl, pH 7.6 (3 CV), and the FSH protein was eluted with 50 mM Tris-HCl, 4 M NaCl, pH 7.6 (6 CV).

Following affinity chromatography a virus inactivation step was performed by incubation of the eluate in 15% 2-propanol for 2 hours. For this purpose the dye affinity chromatography eluate was diluted by factor 2 with 50 mM Tris-HCl, 30% 2-propanol, pH 7.6, resulting in 50 mM Tris-HCl, 15% 2-propanol, 2 M NaCl, pH 7.6. After incubation for 2 hours the virus inactivated dye affinity chromatography eluate was diluted with 20 mM Tris-HCl, pH 7.0 by factor 2.

10 kDa UF/DF:

Ultra- and diafiltration was generally carried out according to standard protocols. Useful UF/DF devices are the SARTOCON ultrafiltration/diafiltration cassettes (polyethersulfone (PESU), 10 kD) from Sartorius (filter area: 14,000 cm$^2$, UF factor: 13-20, DF factor: 8-10, load: 0.1 to 0.5 mg FSH/cm$^2$). Diafiltration with UF/DF devices was generally carried out with ultrafiltration (concentration) factors 13 to 20 and diafiltration factors 8 to 10.

The virus inactivated dye affinity chromatography eluate was diafiltered in Tris-HCl buffer (20 mM Tris-HCl, pH 7.0) and loaded directly onto the cationic membrane adsorber.

Cation Membrane Adsorber Step:

The cation exchange chromatography of the method of the invention was performed using a membrane made from regenerated cellulose and having a chromatographic matrix of sulfonic acid formed on the cellulose backbone. Such a membrane adsorber is available from Sartorius under the trade name SARTOBIND S membrane adsorber. A SARTOBIND S membrane adsorber is a capsule with several membrane layers, on which the ligand is immobilized. Membrane adsorbers have the advantage of short process times and low buffer volumes. The validation costs and time are negligible due to the single-use idea.

The membrane adsorber was equilibrated with 20 mM Tris-HCl, pH 7.0 (200 mL) and the 10 kDa UF/DF retentate (approx. 100 mL) was loaded. The adsorber was post-washed with 20 mM Tris-HCl, pH 7.0 (200 mL).

The processing over the membrane adsorber is in flowthrough mode which reduces process times. Further, no load conditioning is necessary with respect to the next process step (anion exchange chromatography). The product yield in the flowthrough was very good. There was virtually no product loss while processing over a SARTOBIND S module at pH values 6.0, 6.5 and 7.0 in different buffer systems.

The cation membrane adsorber step is very advantageous for HCP (host cell protein) clearance. The yield, at 90 to 95%, is very favourable because the FSH to be purified does not bind to the adsorber at pH 7.0 in 20 mM Tris-HCl buffer system.

Anion Exchange Chromatography Step:

A second anion exchange chromatography was performed using the quaternary ammonium strong anion exchanger resin known in the art as Q SEPHAROSE HP. This resin is available from GE Healthcare.

The AEC column was equilibrated with 20 mM Tris-HCl, pH 7.0 (3 CV). The membrane adsorber flowthrough pool was loaded onto the column (3 CV), and the column was first washed with 20 mM Tris-HCl, pH 7.0 (2 CV), then with 20 mM Tris-HCl, pH 8.5 (3 CV) and finally washed with 20 mM Tris-HCl, 60 mM NaCl, pH 8.5 (5 CV). Then the FSH was eluted with 20 mM Tris-HCl, 130 mM NaCl, pH 8.5 (6 CV).

The Q SEPHAROSE HP eluate has a very high purity comparable to the commercial product GONAL-f® (follitropin alfa).

10 kDa UF:

The 10 kDa ultrafiltration was carried out according to standard protocols using the SARTOCON Ultrafiltration cassette (PESU, 10 kD) from Sartorius (filter area: 3,000 cm$^2$, UF Factor: 10-30, load: 0.2 to 1.0 mg FSH/cm²). Ultrafiltration was generally carried out with ultrafiltration (concentration) factors 10 to 30.

Size Exclusion Chromatography (SEC) Step:

The size exclusion chromatography was performed using SUPERDEX 75 pg, available from GE Healthcare. The column was equilibrated using 50 mM Na—PO₄, pH 7.0 (2 CV). The 10 kDa UF retentate was loaded onto the column (0.025 CV), and the column was post-washed with 50 mM Na—PO₄, pH 7.0 (2 CV).

The SEC eluate has a high purity in the same range as the commercial product GONAL-f® (follitropin alfa).

Nanofiltration:

Finally the SEC eluate was nanofiltered using PLANOVA 15N filters, sold by Asahi Kasei Medical Co., Ltd., the mean pore size being 15 nm. The target load maximum was 2.5 mL/cm². The filtration was performed in accordance to the supplier's protocol.

The purity of the purified FSH was measured by SE-HPLC and SDS-PAGE. The purity and specified impurities of the obtained FSH were as follows:

| | |
|---|---|
| SE-HPLC (Dimers and related substances of higher molecular mass) | <1% |
| SDS-PAGE red. (colloidal) | purity >97% |
| HCP (generic) | <10 ppm |
| DNA | <0.006 pg/IU FSH |

The bioactivity of the recombinant human FSH was determined as at least about 10,000 IU/mg. Preferably the bioactivity of the recombinant human FSH or FSH variant is the range of about 10,000 IU/mg to about 17,000 IU/mg, more preferably the bioactivity is at least about 12,000 IU/mg, and most preferably the bioactivity is at least about 15,000 IU/mg.

SEQUENCE LISTING

SEQ ID No. 1: amino acid sequence of the α-chain of human FSH
SEQ ID No. 2: amino acid sequence of the β-chain of human FSH
SEQ ID No. 3: wild-type nucleic acid sequence coding for the α-chain of human FSH
SEQ ID No. 4: wild-type nucleic acid sequence coding for the β-chain of human FSH
SEQ ID No. 5: codon optimized nucleic acid sequence coding for the β-chain of human FSH
SEQ ID No. 6: codon optimized nucleic acid sequence coding for the α-chain of human FSH

The invention claimed is:

1. A method of purifying a recombinant follicle stimulating hormone (FSH), comprising the steps of subjecting a liquid containing said FSH to:
an anion exchange chromatography,
a hydrophobic interaction chromatography, and
a dye affinity chromatography,
which are performed in any order, wherein the method comprises neither a weak anion exchange chromatography nor a reverse phase chromatography.

2. The method of claim 1, wherein the steps are performed in the following order:
a) an anion exchange chromatography
b) a hydrophobic interaction chromatography, and
c) a dye affinity chromatography.

3. The method of claim 1, wherein the anion exchange chromatography is performed using a strong anion exchange resin having —$N^+(CH_3)_3$ functional groups.

4. The method of claim 1, wherein the hydrophobic interaction chromatography is performed using a resin consisting of cross-linked agarose beads derivatized with phenyl or butyl groups.

5. The method of claim 1, wherein the dye affinity chromatography is performed with 1-amino-4-[4-[[4-chloro-6-(2-sulfoanilino)-1,3,5-triazin-2-yl]amino]-3-sulfoanilino]-9,10-dioxoanthracene-2-sulfonic acid as the ligand, covalently coupled to any matrix.

6. The method of claim 1, wherein the chromatography is performed using a Tris-HCl/sodium chloride buffer as eluent at a pH in the range between 7.0 and 9.0.

7. The method of claim 1, the method further comprising a cation exchange chromatography.

8. The method of claim 7, wherein the cation exchange chromatography is performed with a strong acidic cation exchanger sulfonic acid fixed on a membrane.

9. The method of claim 7, wherein the steps are performed in the following order:
   a) anion exchange chromatography,
   b) a hydrophobic interaction chromatography,
   c) a dye affinity chromatography, and
   d) a cation exchange chromatography.

10. The method of claim 1, further comprising a further anion exchange chromatography.

11. The method of claim 10, wherein the anion exchange chromatography is performed using a strong anion exchange resin having —N$^+$(CH$_3$)$_3$ functional groups, or a resin having similar characteristics.

12. The method of claim 10, wherein the anion exchange chromatography is performed using a Tris-HCl/sodium chloride buffer as eluent at a pH in the range between 7.0 and 9.0.

13. The method of claim 10, wherein the steps are performed in the following order:
   a) a first anion exchange chromatography,
   b) a hydrophobic interaction chromatography,
   c) a dye affinity chromatography,
   d) an optional cation exchange chromatography, and
   e) a second anion exchange chromatography.

14. The method of claim 1, the method further comprising a size exclusion chromatography.

15. The method of claim 14, wherein the size exclusion chromatography is performed using a matrix of spherical composite of cross-linked agarose and dextran.

16. The method of claim 14, wherein the steps are performed in the following order:
   a) a first anion exchange chromatography,
   b) a hydrophobic interaction chromatography,
   c) a dye affinity chromatography,
   d) an optional cation exchange chromatography,
   e) an optional second anion exchange chromatography, and
   f) a size exclusion chromatography.

17. The method of claim comprising the following steps in the following order:
   a) a first anion exchange chromatography,
   b) a hydrophobic interaction chromatography,
   c) a dye affinity chromatography,
   d) a membrane cation exchange,
   e) a second anion exchange chromatography, and
   f) a size exclusion chromatography.

18. The method of claim 1, further comprising one or more ultrafiltration and/or nanofiltration steps.

19. The method of claim no metal ion affinity chromatography is performed.

20. The method of claim 1, wherein no immunoaffinity chromatography is performed.

21. The method of claim 1, wherein the FSH has an α-subunit according to SEQ ID NO: 1 and a β-subunit according to SEQ ID NO: 2.

22. An FSH obtained by the method according to claim 21 comprising less than 1% dimers and related substances of higher molecular mass. less than 10 ppm generic host cell protein (HCP), less than 0.006 pg/IU FSH DNA, and having a purity of more than 97%.

23. A pharmaceutical composition comprising the FSH according to claim 22 as well as a pharmaceutically acceptable excipient.

24. A method for treating fertility disorders comprising a step of administering the FSH according to claim 22 to a patient.

25. A method for treating fertility disorders comprising a step of administering the pharmaceutical composition according to claim 23 to a patient.

26. A method of producing a recombinant human FSH comprising the steps of
   a) generating a CHO cell clone which produces the recombinant human FSH from one or more recombinant nucleic acid molecules which code for the α-chain and the β-chain of human FSH, thereby obtaining CHO host cells,
   b) cultivating of the CHO host cells under suitable conditions, thereby obtaining a cell culture containing a recombinant human FSH, and
   c) purifying the recombinant human FSH from the cell culture according to the method of claim 1.

* * * * *

SEQUENCE LISTING

```
<160> NUMBER OF SEQ ID NOS: 6

<210> SEQ ID NO 1
<211> LENGTH: 116
<212> TYPE: PRT
<213> ORGANISM: Homo sapiens
<220> FEATURE:
<221> NAME/KEY: CHAIN
<222> LOCATION: (1)..(116)
<223> OTHER INFORMATION: alfa-chain of human FSH

<400> SEQUENCE: 1

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

<210> SEQ ID NO 2
<211> LENGTH: 129
<212> TYPE: PRT
<213> ORGANISM: Homo sapiens
<220> FEATURE:
<221> NAME/KEY: CHAIN
<222> LOCATION: (1)..(129)
```

<223> OTHER INFORMATION: beta-chain of human FSH

<400> SEQUENCE: 2

```
Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu
```

<210> SEQ ID NO 3
<211> LENGTH: 369
<212> TYPE: DNA
<213> ORGANISM: Homo sapiens
<220> FEATURE:
<221> NAME/KEY: misc_feature
<223> OTHER INFORMATION: wild-type nucleic acid sequence coding for the
      alfa-chain of human FSH

<400> SEQUENCE: 3

```
cttaattaag ccgccagcat ggattactac agaaaatatg cagctatctt tctggtcaca    60
ttgtcggtgt ttctgcatgt tctccattcc gctcctgatg tgcaggattg cccagaatgc   120
acgctacagg aaaacccatt cttctcccag ccgggtgccc caatacttca gtgcatgggc   180
tgctgcttct ctagagcata tcccactcca ctaaggtcca agaagacgat gttggtccaa   240
aagaacgtca cctcagagtc cacttgctgt gtagctaaat catataacag ggtcacagta   300
atgggggggtt tcaaagtgga gaaccacacg gcgtgccact gcagtacttg ttattatcac   360
aaatcttaa                                                            369
```

<210> SEQ ID NO 4
<211> LENGTH: 474
<212> TYPE: DNA
<213> ORGANISM: Homo sapiens
<220> FEATURE:
<221> NAME/KEY: misc_feature
<223> OTHER INFORMATION: wild-type nucleic acid sequence coding for the
      beta-chain of human FSH

<400> SEQUENCE: 4

```
aggatccccg ggctacctcc ccgcggggag gcgcgcccct taattaagcc gccaccatga    60
agacactcca gttttctctc ctttctctgtt gctggaaagc aatctgctgc atagctgtg   120
agctgaccaa catcaccatt gcaatagaga aagaagaatg tcgtttctgc ataagcatca   180
acaccacttg gtgtgctggc tactgctaca ccagggatct ggtgtataag acccagccaa   240
gcccaaaaat ccagaaaaca tgtaccttca aggaactggt atatgaaaca gtgagagtgc   300
ccggctgtgc tcaccatgca gattccttgt atacataccc agtggccacc cagtgtcact   360
```

```
gtggcaagtg tgacagcgac agcactgatt gtactgtgcg aggcctgggg cccagctact    420
gctcctttgg tgaaatgaaa gaataaacat gccatggcat gcgagctcga attc          474

<210> SEQ ID NO 5
<211> LENGTH: 471
<212> TYPE: DNA
<213> ORGANISM: Artificial
<220> FEATURE:
<223> OTHER INFORMATION: codon-optimized nucleic acid sequence coding
      for the beta-chain of human FSH

<400> SEQUENCE: 5 aggatcccg ggtacctccc cgcggggagg cgcgccccctt aattaagccg ccaccatgaa     60
gaccctgcag ttcttcttcc tgttctgctg ctggaaggcc atctgctgca acagctgcga   120
gctgaccaac atcaccatcg ccatcgagaa ggaggagtgc aggttctgca tcagcatcaa   180
caccacctgg tgcgccggat actgctacac cagggacctg gtgtacaagg accccgccag   240
gcccaagatc cagaagacct gcaccttcaa ggagctggtg tacgagaccg tgagggtgcc   300
cggctgcgcc caccacgccg acagcctgta cacctacccc gtggccaccc agtgccactg   360
cggcaagtgc gacagcgaca gcaccgactg caccgtgagg ggcctgggcc ccagctactg   420
cagcttcggc gagatgaagg agtaatgacc atggcatgcg agctcgaatt c             471

<210> SEQ ID NO 6
<211> LENGTH: 372
<212> TYPE: DNA
<213> ORGANISM: Artificial
<220> FEATURE:
<223> OTHER INFORMATION: codon-optimized nucleic acid sequence coding
      for the alfa-chain of human FSH

<400> SEQUENCE: 6
cttaattaag ccgccagcat ggactactac aggaagtacg ccgccatctt cctggtgacc     60
ctgagcgtgt tcctgcacgt gctgcacagc gccccagacg tgcaggactg ccccgagtgc   120
accctgcagg agaacccatt cttcagccag cccggagccc ccatcctgca gtgcatgggc   180
tgctgcttca gcagggccta ccccacccc ctgaggagca agaagaccat gctggtgcag   240
aagaacgtga ccagcgagag cacctgctgc gtggccaaga gctacaacag ggtgaccgtg   300
atgggcggct tcaaggtgga gaaccacacc gcctgccact gcagcacctg ctactaccac   360
aagagctaat ga                                                         372
```